US00PP37670P2

(12) United States Plant Patent
Byrne et al.

(10) Patent No.: US PP37,670 P2
(45) Date of Patent: Sep. 8, 2026

(54) PEACH TREE NAMED 'TRH3A17'

(50) Latin Name: *Prunus persica*
Varietal Denomination: TRH3A17

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/336,361

(22) Filed: Sep. 22, 2025

(51) Int. Cl.
*A01H 6/74* (2018.01)

(52) U.S. Cl.
USPC ..... Plt./197
CPC ..... *A01H 6/7463* (2018.05)

(58) Field of Classification Search
USPC ..... Plt./197
CPC ..... A01H 5/0868
See application file for complete search history.

(56) References Cited

PUBLICATIONS

U.S. Appl. No. 19/336,141, filed Sep. 22, 2025, Byrne et al.
U.S. Appl. No. 19/336,148, filed Sep. 22, 2025, Byrne et al.
U.S. Appl. No. 19/336,164, filed Sep. 22, 2025, Byrne et al.
U.S. Appl. No. 19/336,169, filed Sep. 22, 2025, Byrne et al.
U.S. Appl. No. 19/336,358, filed Sep. 22, 2025, Byrne et al.
U.S. Appl. No. 19/336,363, filed Sep. 22, 2025, Byrne et al.
U.S. Appl. No. 19/336,365, filed Sep. 22, 2025, Byrne et al.
U.S. Appl. No. 19/336,368, filed Sep. 22, 2025, Byrne et al.
U.S. Appl. No. 19/336,370, filed Sep. 22, 2025, Byrne et al.
U.S. Appl. No. 19/336,372, filed Sep. 22, 2025, Byrne et al.
U.S. Appl. No. 19/336,375, filed Sep. 22, 2025, Byrne et al.
U.S. Appl. No. 19/336,377, filed Sep. 22, 2025, Byrne et al.
U.S. Appl. No. 19/336,380, filed Sep. 22, 2025, Byrne et al.
U.S. Appl. No. 19/336,383, filed Sep. 22, 2025, Byrne et al.
U.S. Appl. No. 19/336,385, filed Sep. 22, 2025, Byrne et al.
Community Plant Variety Office, Certificate on the Grant of Community Plant Variety Rights No. 25391, with Descriptive Card of Characteristics of the Victor Variety, Breeder's Ref.: FIR-180-ZONA, published Aug. 15, 2009.
Raseira et al.. 2010. Pessegueiro: Cultivar BRS Kampai. Rev, Bras. Frutic. 32 (4): 1275-1278, protected Certificado de Proteção de Cultivar, República Federativa do Brasil, No. 20100059, Sep. 9, 2009.
Rawandoozi, May 2019, QTL Mapping Through Pedigree-Based Analysis for Six Phenological and Quality Traits in Peach. Dissertation for Doctor of Philosophy. Texas A&M University.

*Primary Examiner* — Kent L Bell
(74) *Attorney, Agent, or Firm* — Dentons US LLP

(57) ABSTRACT

Disclosed is a new variety of *Prunus persica* named 'TRH3A17'. This new variety, which requires approximately 350 chilling units of dormancy, is a peach tree of very early season maturity, which produces subacid, yellow-fleshed fruit that are firm, with a 50-80% red-orange blush over a yellow-green ground color, and suitable for the fresh market.

5 Drawing Sheets

Latin name of the genus and species of the plant claimed: *Prunus persica.*

Variety denomination: 'TRH3A17'.

BACKGROUND OF THE INVENTION

This invention relates to a peach tree and, more specifically, to a peach tree referred to as a variety of *Prunus persica* named 'TRH3A17' which requires approximately 350 chilling units of dormancy, produces a firm clingstone, subacid, yellow-fleshed peach that matures very early in the season. The present peach tree was the result of an ongoing Stone Fruit Breeding Program at College Station, Brazos County, Texas. To this end, controlled crosses are made each year to produce seedling populations from which improved progenies are evaluated and selected. 'TRH3 A17' was selected from a population of seedlings that resulted from embryo rescued seed from a cross done in 2007 between the early ripening. yellow-fleshed peach 'Victor' (not patented in US, Byrne, D.H. 2009. 'Victor'. Plant Breeders Rights, European Union. No. 25391; protected in Europe) as the female and the subacid, white-fleshed peach 'BRS Kampai' (not patented in US, Raseira, M. B. Nakasu, B. Ueno and C.

Scaranari. 2010. Pessegueiro: Cultivar BRS Kampai. Rev, Bras. Frutic. 32 (4):1275-1278, protected Certificado de Proteção de Cultivar, República Federativa do Brasil, No. 20100059, Sep.09, 2009; protected in Brazil) as the pollen parent. 'Victor' is a cross between the non-patented low chill subtropical yellow-flesh peach cultivar 'Tropic Beauty' (Rouse and Sherman, 1989) and the non-patented medium chill early-ripening yellow-flesh peach 'Goldprince' (Okie, 1993). 'BRS Kampai' was developed in Pelotas, RS, Brazil. This subacid white-flesh peach resulted from a cross between two non-patented low chill peaches: the subacid white-flesh peach 'Chimaritta' and the yellow-flesh peach 'Flordaprince' (Raseira et al., 2010). Resulting seedlings from this cross between 'Victor' x 'BRS Kampai' were planted in 2008 in Floresville, Texas.

'TRH3A17' was marked for subsequent observation and noted as having exceptional characteristics in 2010. Two-year and older trees of the variety were subsequently evaluated during the 2012 through 2020 fruit growing seasons in Texas (Pleasanton, Fairfield and Somerville). 'TRH3 A17' differs from its pollen parent 'BRS Kampai' as it blooms ~ 2 weeks later and ripens ~ 3 weeks before and has yellow flesh as compared to the white flesh of its pollen parent. This new subacid, yellow-flesh peach exhibits potential to be commercialized in regions that have chilling requirements that are low. 'TRH3A17' differs from its female parent, 'Victor' as it blooms 2-3 days before, ripens 3-5 days before and has subacid flesh and reniform glands as compared to traditional acid flesh and globose glands of its female parent.

'TRH3A17' was bud grafted onto virus-free 'Nemaguard' (not patented, The Brooks and Olmo Register of Fruit and Nut Varieties, 3rd Ed., American Society of Horticultural Science Press, Alexandria, VA, 1997) peach rootstock at the nursery site in Oakdale, CA. The variety was subsequently planted at experimental orchards in three sites in Texas (Pleasanton, Somerville and Fairfield). Fruit from the resulting propagation has been evaluated during the period from 2012 to 2020 fruit seasons. This evaluation clearly demonstrated that the re-propagated trees were true to the characteristics of the original seedling in all observable aspects.

SUMMARY OF THE INVENTION

The 'TRH3A17' peach is characterized by producing fruit that ripens in the very early season; is a subacid, yellow fleshed, firm peach has an orange-red blush (50-80%) over the yellow-green ground color of the fruit surface. In this regard, the present variety of peach tree bears fruit that are ripe for commercial harvesting and shipment in late April to the first week of May, when the fruit is grown in medium chill zone of Texas. 'TRH3A17' differs from its pollen parent 'BRS Kampai' as it blooms ~ 2 weeks later and ripens ~ 3 weeks before and has yellow flesh as compared to the white flesh of its pollen parent. 'TRH3A17' differs from its female parent, 'Victor' as it blooms 2-3 days before, ripens 3-5 days before and has subacid flesh and reniform glands as compared to traditional acid flesh and globose glands of its female parent. This new subacid, yellow-flesh peach exhibits potential to be commercialized in regions that have chilling requirements that are low. 'TRH3A17' ripens very early and has yellow-flesh as does 'TexFirst' (patented, U.S. Plant Pat. No. 26,119) but differs from it as it has subacid versus a traditional acid flesh flavor and blooms about 10 days later than 'TexFirst'. 'TRH3A17' differs from the yellow-fleshed peach, 'TexKing' (patented, U.S. Plant Pat. No. 14,627) as it has reniform versus globose glands, has subacid versus a traditional acid flesh flavor, blooms 10 days before and ripens about 2 weeks before 'TexKing'. 'TRH3 A17' differs from the low acid peach 'White Delight One' (not patented, US App. Pub. No. 2016/0205833 P1, abandoned) as it has showy versus non showy flowers, has reniform versus globose glands, blooms about 2 weeks earlier and ripens one week earlier than 'White Delight One'.

BRIEF DESCRIPTION OF THE DRAWINGS

This new variety of peach tree is illustrated by the accompanying photographs of 3-year to 5-year old plants grown in College Station and Fairfield, Texas, as provided in FIGS. 1-5. These photographs show the plant's typical fruit, foliage, and flowers, and the colors shown are as true as can be reasonably obtained by conventional photographic procedures.

DETAILED BOTANICAL DESCRIPTION

Figure 1:
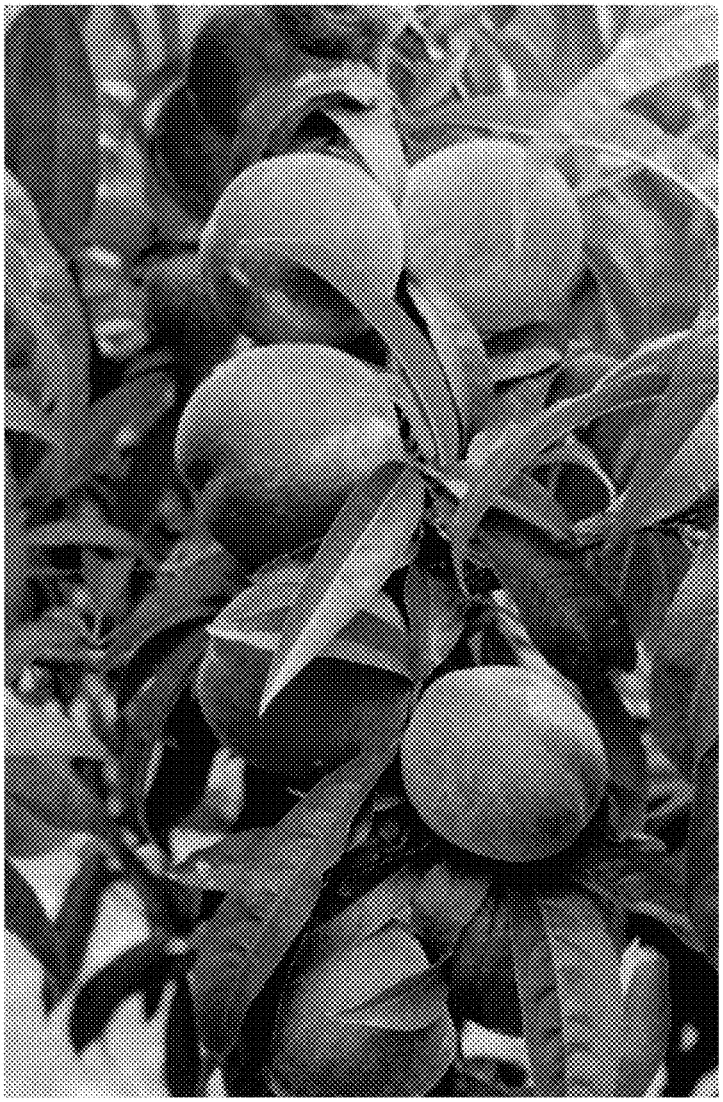
FIG. 1 Fruit of 'TRH3A17'. The fruit was harvested on Apr. 24, 2018 on a tree in the experimental orchard in College Station, TX.
Figure 2:
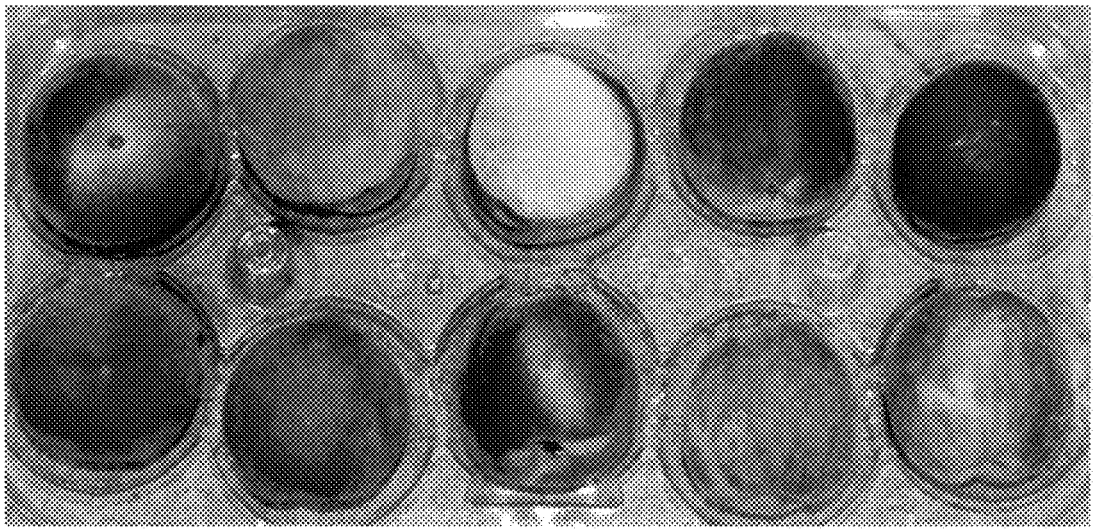
FIG. 2 'TRH3A17' fruit harvested in May 2018 in Fairfield, Texas showing external and internal coloration.
Figure 3:
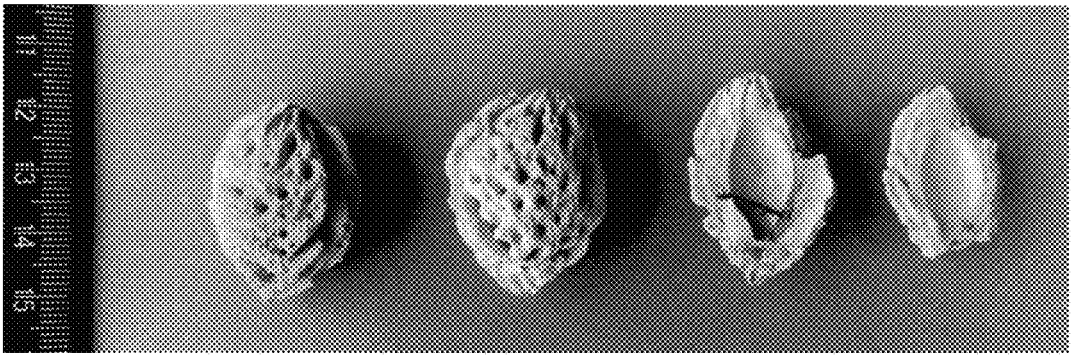
FIG. 3 Photograph of the endocarps of the 'TRH3A17' peach. The ruler is in centimeters.
Figure 4:
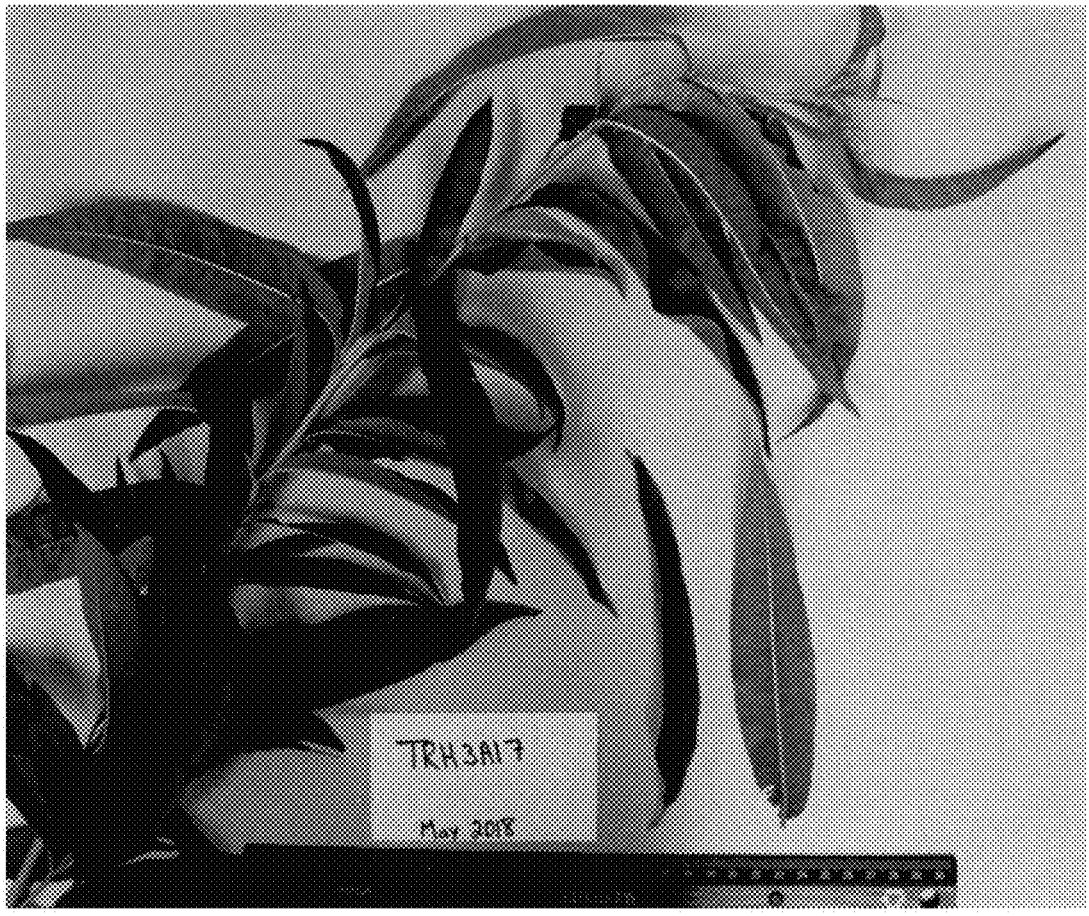
FIG. 4 A stem showing the leaves of the 'TRH3A17' peach. The ruler is in centimeters.
Figure 5:
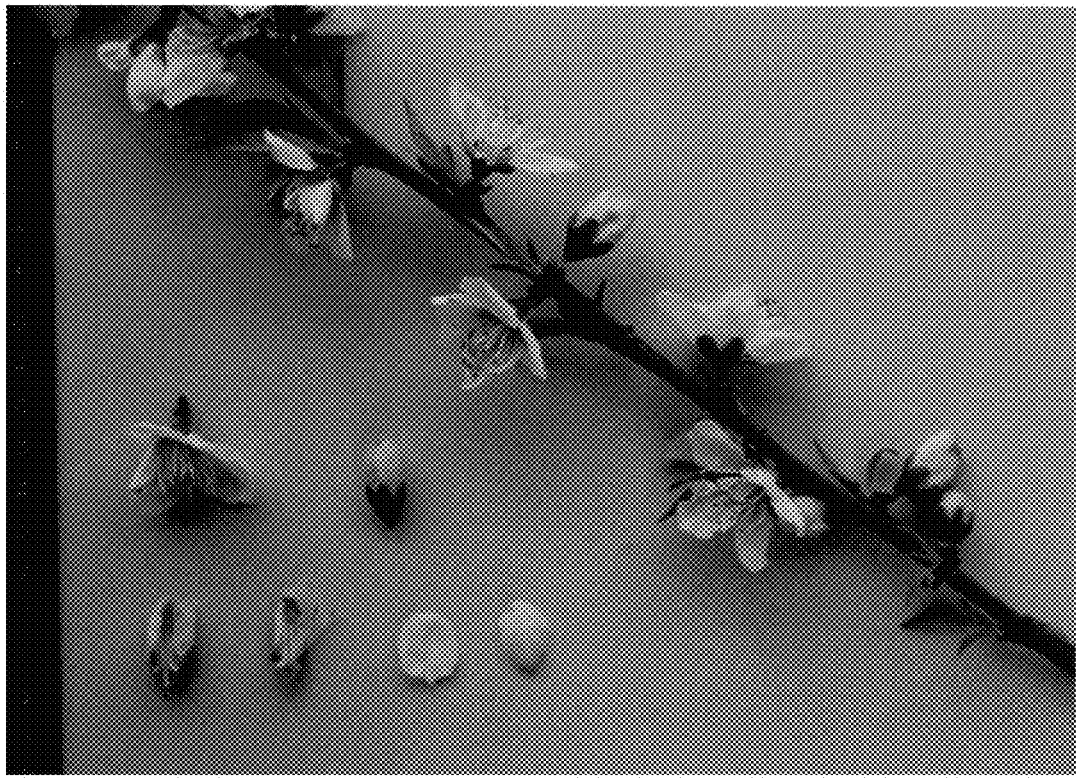
FIG. 5 A stem showing the flowers of the 'TRH3 A17' peach. The ruler is in centimeters.

Referring more specifically to the pomological details of this new and distinct variety of peach tree, the following has been observed under the ecological conditions prevailing at the experimental orchards in the medium chill zone of Texas. All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally medium to medium large as compared to other common peach cultivars ripening in the early season of maturity.

*Height*.—8-10 feet (2.4-3 m) at the end of the 2020 growing season.

*Width*.—4-5 feet width (1.2-1.5 m) at the end of the 2020 growing season.

*Productivity*.—Produces annually in the medium chill zone of Texas without alternate bearing if temperatures of 28° F. or lower are not experienced during bloom. Trees are self-fertile and must be fruit thinned to avoid limb breakage and obtain optimal fruit size. The recommended fruit spacing for early to mid-season ripening fresh market peach cultivars for a full crop is one fruit every 6-8" of one-year old fruiting wood. Trees often set several times the number of fruit needed for a full crop load.

*Shape*.—The 'TRH3A17' peach has been trained in an open center configuration and exhibits a semi spreading growth type as seen in peach varieties 'Texprince' (U.S. Plant Pat. No. 14,629) and 'TexKing' (U.S. Plant Pat. No. 14,627).

*Current season growth*.—The current season growth for the new variety was approximately 3 to 5 feet (0.9-1.5 m). Medium to high vigor as compared to other commercial cultivars grown in the medium chill zone. Regularity of Bearing — Regular, in the absence of temperatures below 28° F. during bloom under the typical conditions of the medium chill zone of Texas.

Trunk:

*Size*.—Approximately 1.75 to 2 inches (4.4 to 5.1 cm) in diameter and 6 to 6.5 inches (15.2 to 16.5 cm) in circumference when measured at approximately 12 inches (30.5 cm) above the soil level, at the end of the 2020 growing season on a five-year old tree.

*Bark texture*.—Considered moderately rough with numerous folds of papery scarf-like skin being present. Bark Coloration — Variable, colors (RHS2001) present are 165A, 166A, 174A, 175A, 176A, 176B and 177A of the Greyed-Orange Group, 200D of the Brown Group, and 201A, 201B, 201C and 201D of the Grey Group.

Branches:

*Thickness*.—Average (about 1.6 to 2.4 cm in diameter as measured 10 cm from the trunk on a five-year old tree) as compared to other varieties.

*Surface texture*.—Average and appearing furrowed on wood that is several years old.

*Lenticels*.—Numerous raised, oval lenticels present. The lenticels range in size from approximately 3 to 6 mm in width and were approximately 2 mm in height.

*Current season shoots*.—Surface texture — Substantially glabrous.

*Internode length*.—Approximately 1.8 to 2.8 cm as measured in the middle of a current season stem.

*Color of mature branches*.—The predominant colors (RHS2001) are 166A, 175A, 175B, 176A, 176B, 176C, 176D and 177A of the Greyed-Orange Group, 198A, 198B, 198C, and 198D of the Greyed-Green Group and 200C of the Brown Group. Current Season Shoots — Color (RHS2001) — Light-medium green (144A, 144B, N144C and 146D of Yellow-Green Group) with some reddish-brown coloration appearing on exposed surface of the shoots (166A and 176A of the Greyed-Orange Group).

Leaves:

*Size*.—Considered moderate to moderately large for the species. Leaf measurements have been taken from vigorous upright current season growth approximately at mid-shoot.

*Leaf length*.—Approximately 143 to 166 mm.

*Leaf width*.—Approximately 38 to 40 mm.

*Leaf thickness*.—Less than 1 mm.

*Leaf form*.—Lanceolate.

*Leaf tip form*.—Acuminate.

*Leaf upper surface color* (*RHS*2001).—Green varying among 137A and 137B of the Green Group and 146A of the Yellow-Green Group.

*Leaf lower surface color* (*RHS*2001).—Green varying among 146A and 147B of the Yellow-Green Group.

*Leaf lower mid-vein color* (*RHS*2001).—Light yellow green, approximated by N144A and 145C of the Yellow-Green Group.

*Leaf margins*.—Form — Considered crenate. Uniformity — Considered generally uniform.

*Leaf petioles*.—Size — Considered medium to long. Length — Approximately 9 to 14 mm. Thickness — Approximately 2 mm. Texture — Glabrous. Color (RHS2001) — Light yellow-green, similar to N144A and 145C of the Yellow-Green Group.

*Leaf glands*.—Size — Approximately 1-1.5 mm in height and 1 mm in width. Number — Generally 2 per leaf. Type — Reniform. Color (RHS2001) — Light yellow-green, similar to 144B, N144A, N144B, N144C, N144D, 145A, 145B, 146C and 146D of the Yellow-Green Group with occasional browning (165A and 166B of the Greyed-Orange Group).

*Leaf stipules*.—Length — Approximately 13.8 to 14.1 mm. Width — Less than 1 mm. Form — Lanceolate. Color (RHS2001) — Green, 144A of the Yellow-Green Group with reddish brown tips 178B, 179A, 180A, 181A and 181B of the Greyed-Red Group. Color is similar on both surfaces. The stipules early deciduous.

*Ratio of wood* (*leaf*) *buds to flowering buds*.—One to two flower buds per vegetative bud.

Flowers:

*Floral buds*.—

*General*.—The floral buds are considered to be conic in form, and slightly appressed relative to the bearing shoot.

*Color* (*RHS*2001).—Dormant buds are medium brown, (approximately 165A of the Greyed-Orange Group, 199A and N199B of the Grey-Brown Group and 200D of the Brown Group). The buds are considered hardy in the medium chill zone of Texas.

*Dormant bud length*.—Approximately 3 to 5 mm.

*Dormant bud width*.—Approximately 2 mm.

*Blooming type*.—Considered quite early in relation to other peach cultivars commonly growing in the medium chill zone of Texas. Date of full bloom was between February 1st and February 22$^{nd}$ (mean February 10$^{th}$) during the period between 2012 and 2020. It bloomed with or a little before its female parent 'Victor' (mean February 12$^{th}$), about one week after the low chill peach, 'TexFirst' (mean February 4$^{th}$ (Byrne, D. H. and N. Anderson. 2012. 'TexFirst', An early ripening low chill peach for the subtropics. HortScience 47:1803-1804. U.S. Plant Pat. No. 26,199, 24 November 2015) and a week before the medium chill peach 'FlordaKing' (mean February 16$^{th}$) (not patented; Andrews, C.P. 1979. 'Flordaking' peach. HortScience 14(1):81-82).

*Flower type*.—Showy.

*Flower size*.—Flower diameter at full bloom is approximately 33 to 37 mm.

*Bloom quantity*.—Considered abundant.

*Flower bud frequency*.—Normally 1 to 2 per node.

*Petal size*.—General — Considered medium to medium large for the species. Width — Approximately 14 to 16 mm. Length — Approximately 19 mm.

*Petal form*.—Broadly ovate.

*Petal number*.—Nearly always 5.

*Petal abaxial/adaxial color* (*RHS*2001).—Light to medium pink when young (62A, 62B and 73D of the Red-Purple Group).

*Petal claw*.—Form — The claw is considered truncate in shape. Length — Approximately 1 to 2 mm. Width — Approximately 1 mm.

*Petal margins*.—Generally considered variable, from nearly smooth to slightly undulate.

*Petal apex*.—Generally — The petal apices appear rounded.

*Flower pedicel*.—Length — Considered moderately long, and having an average length of approximately 4 to 5 mm. Thickness — Considered average, approximately 1 mm. Color (RHS2001) — Medium green (144C and 145A of the Yellow-Green Group).

*Floral nectaries*.—Color (RHS2001) — Medium to dark orange (25A, N25A, N25B, 28A and 28B of the Orange Group).

*Sepals*.—

*Sepal number*.—Five per flower. Surface Texture — The surface has a short, fine, wooly texture. Size — Average Length 6.0 mm; Width 4.0 mm. Form — Ovate. Lower Sepal Color (RHS2001) — Maroon with green and white (approximately 53A, 53B of the Red Group; 144A and 146C of the Yellow-Green Group; 155A, 155B, 155C and 155D of the White Group; 178 A and 178B of the Greyed-Red Group and 183A, 183B, 187B and 187C of the Greyed-Purple).

*Floral cup* (*hypanthium*).—Surface Texture — Generally glabrous. Color (RHS2001) — Maroon with green (approximately 53A, and 53B of the Red Group; 144A and 146C of the Yellow-Green Group; 178A and 178B of the Greyed-Red Group and 183A, 183B, 187B and 187C of the Greyed-Purple Group).

*Anthers*.—Color (RHS2001) — Dark orange (approximately 25A, 25B, N25A and N25B of the Orange Group). Color (RHS2001) — Dark orange (approximately 25A, 25B, N25A and N25B of the Orange Group).

*Pollen production*.—Pollen is abundant and is a medium-yellow color (RHS2001) (approximately 2A, 2B, 3A, 3B, 4A, 4B and 5C of the Yellow Group).

*Filaments*.—

*Size*.—Variable in length, approximately 15 to 19 mm, with the filaments approximately equal to the pistil. Anthers slightly below the petal height. Color (RHS2001) — White (approximately 155A, 155B, 155C and 155D of the White Group) and darkening with advanced maturity.

*Pistil*.—General — Approximately equal to the general anther height. Stigmas slightly below the petal height. Length — Approximately 17 to 19 mm, including the ovary. Color (RHS2001) — Considered white to very light green when young (approximately 155A, 155B, 155C and 155D of the White Group and 157A, 157B, 157C and 157D) of the Green-White Group and becoming slightly darker with advancing senescence.

*Surface texture*.—The variety has a pubescent ovary and style.

Fruit:

*Maturity when described*.—The present variety of fruit is described, as it would be found in its firm ripe condition at full commercial maturity. Under the ecological conditions prevailing in medium chill zone of Texas. First Picking: April 26. Last Picking: May 6.

*Size*.—General — Medium to medium large for the season and considered uniform. Average Cheek Diameter — Approximately 59 to 64 mm. Average Suture Diameter — Approximately 59 to 65 mm. Average Axial Diameter — Approximately 54 to 60 mm.

*Fruit form*.—Generally considered round.

*Fruit suture*.—Generally, the suture appears as a thin line that extends from the base to the apex, and occasionally appears deeper at the apex, forming a shallow basin at the apical point. No apparent callusing or stitching exists along the suture line. Color (RHS2001) — 34A, 34B and N34A of the Orange-Red Group; 42B, 45A, 53A, 53B of the Red Group and 183A, 183B, 187B and 187C of the Greyed-Purple Group.

*Ventral surface*.—Form — Considered uniform.

*Stem cavity*.—Size — Considered moderately shallow for the species. Width — Approximately 13 to 18 mm. Length — Approximately 18 to 23 mm. Depth — Approximately 7 to 10 mm. Form — Considered flat.

*Fruit base*.—Flat.

*Fruit apex*.—Flat.

*Fruit stem*.—Length — 10 to 13 mm. Thickness — Approximately 3 to 4 mm. Color (RHS2001) — Green, 144A, 144B and N144C of the Yellow-Green Group.

*Fruit skin*.—Generally considered medium or average in thickness. Surface Texture — Light, short pubescence. Skin Acidity — Considered neutral. Tenacious to Flesh — Yes at commercial maturity. Tendency to Crack — Not observed.

*Skin color*.—Generally — Variable, with approximately 50-80% of the fruit surface covered with an orange red blush. The fruit skin over color pattern varies from striped to marbled. Blush Color (RHS2001) — 34A, 34B and N34A of the Orange-Red Group; 42B, 45A, 53A, 53B of the Red Group and 183A, 183B, 187B and 187C of the Greyed-Purple Group. Skin Ground Color (RHS2001) — Similar to 1B, 1C, and 1D of the Yellow-Green Group and 151C and 154B of the Yellow-Green Group.

*Flesh color* (*RHS*2001).—11B and 12C of the Yellow Group and 14C and 15D of the Yellow-Orange Group. Anthocyanin intensity in the flesh is generally very weak to weak next to the skin, centrally and next to the pit.

*Flesh fibers*.—Present throughout the flesh.

*Stone cavity color* (*RHS*2001).—11B and 12C of the Yellow Group and 14C and 15D of the Yellow-Orange Group.

*Flesh texture*.—Generally, the flesh is considered firm and fine at commercial maturity.

*Ripening*.—Generally the fruit of the present variety ripens evenly.

*Flavor*.—Considered sweet (average Brix 10.9) and subacid.

Stone:

*Attachment*.—Clingstone at commercial maturity.

*Stone size*.—Length — Approximately 32 to 34 mm. Width — Approximately 22 to 25 mm. Thickness — Approximately 17 to 18 mm.

*Fibers*.—Generally a few fibers are attached along the entire surface of the stone.

*Stone shape*.—Elliptical.

*Stone base angle*.—Considered medium.

*Stone apex angle*.—Narrow.

*Stone surface*.—Surface Texture — Variable, with single pits, rosettes of pits and chains of pits.qj Ridges — Numerous fine ridges are present basally and converge towards the base of the stone.

*Ventral edge*.—Large and truncated.

*Dorsal edge*.—Shape — Grooved and having moderately rough edges.

*Stone color* (*RHS*2001).—The color of the dry stone is light brown 158A, 158B of the Yellow-White Group and 159A, 159B of the Orange-White Group. The color of the inside surface of the endocarp is primarily 158A of the Yellow-White Group and 164D of the Greyed-Orange Group.

*Tendency to split*.—Splitting is relatively uncommon.

*Kernel*.—Fresh kernels have an elliptical shape, fill the endocarp at harvest and measures approximately 3-4 mm in thickness, 9-11 mm in width, and 15-18 mm in length. The colors (RHS2001) of the fresh kernels are primarily 155B, 155C and 155D of the White Group and 158B, 158C and 158D of the Yellow-White Group. When dried the shriveled kernels measure approximately 1 mm in thickness, 7-8 mm in width, and 14-15 mm in length. The colors (RHS2001) of the shriveled kernels are primarily 158A of the Yellow-White Group, 161D of the Greyed-Yellow Group, 164A, 164B, 164C and 165B of the Greyed-Orange Group and N199D of the Greyed-Brown Group.

*Use*.—The subject variety, 'TRH3A17', is considered to be a peach tree of early-season maturity, which produces fruit which are very firm, subacid, yellow-fleshed peaches that have a 50-80% red-orange blush over a yellow-green ground color and which are useful for the fresh fruit market.

*Keeping quality*.—Retains flavor and texture after 14 days of refrigeration at 3-5° C.

*Resistance to insects and disease*.—Moderately susceptible to bacterial leaf spot [*Xanthomonas arboricola* pv. *pruni* (E. F. Smith) Dye] as is the medium chill cultivar 'TexKing'. Otherwise, no atypical resistances/susceptibilities were noted under normal cultural practices to date.

*Shipping quality*.—Retains firmness and eating quality without the development of internal breakdown after 14 days of refrigeration at 3-5° C.

Although the new variety of peach tree possesses the described characteristics when grown under the ecological conditions prevailing near Pleasanton, Somerville and Fairfield, TX in the medium chill zone, it will be understood that variations of the usual magnitude and characteristics incident to the changes in growing conditions, fertilization, pruning, and pest control are to be expected.

What is claimed is:

1. A new and distinct variety of peach tree named 'TRH3A17', as illustrated and described herein.

* * * * *